(12) United States Patent
Inoue

(10) Patent No.: US 10,849,572 B2
(45) Date of Patent: Dec. 1, 2020

(54) NUCLEAR MEDICAL DIAGNOSIS APPARATUS AND POSITION CORRECTION METHOD

(71) Applicant: CANON MEDICAL SYSTEMS CORPORATION, Otawara (JP)

(72) Inventor: Motohiro Inoue, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 20 days.

(21) Appl. No.: 16/407,630

(22) Filed: May 9, 2019

(65) Prior Publication Data

US 2019/0343469 A1 Nov. 14, 2019

(30) Foreign Application Priority Data

May 10, 2018 (JP) .................. 2018-091244

(51) Int. Cl.

| | | |
|---|---|---|
| *G01J 1/42* | (2006.01) | |
| *A61B 6/03* | (2006.01) | |
| *G01T 1/29* | (2006.01) | |
| *A61B 5/00* | (2006.01) | |
| *G06T 11/00* | (2006.01) | |
| *A61B 90/00* | (2016.01) | |

(52) U.S. Cl.
CPC ............ *A61B 6/037* (2013.01); *A61B 5/0077* (2013.01); *A61B 90/39* (2016.02); *G01T 1/2985* (2013.01); *G06T 11/003* (2013.01); *A61B 2090/3937* (2016.02); *G06T 2211/424* (2013.01)

(58) Field of Classification Search
CPC ....... A61B 6/037; A61B 5/0077; A61B 90/39; A61B 2090/3937; A61B 6/4411; A61B 6/4258; A61B 6/547; A61B 6/032; A61B 6/4417; G01T 1/2985; G06T 11/003; G06T 2211/424; G06T 11/005
See application file for complete search history.

(56) References Cited

U.S. PATENT DOCUMENTS

| | | | | |
|---|---|---|---|---|
| 6,239,438 | B1 * | 5/2001 | Schubert | .................. G01T 1/17 250/363.02 |
| 8,313,238 | B2 | 11/2012 | Takahashi | |
| 2006/0124855 | A1 * | 6/2006 | Gagnon | ................. A61B 6/037 250/370.09 |
| 2008/0247506 | A1 * | 10/2008 | Maschke | .................. A61B 6/12 378/15 |
| 2016/0038029 | A1 * | 2/2016 | Darne | .................. A61B 5/0071 600/427 |
| 2016/0247293 | A1 * | 8/2016 | Beylin | .................... A61B 6/037 |
| 2016/0278731 | A1 * | 9/2016 | Babic | .................. A61B 6/4441 |
| 2017/0086680 | A1 * | 3/2017 | Hirata | ................. A61B 5/0091 |
| 2017/0112416 | A1 * | 4/2017 | Hao | ...................... A61B 5/0037 |
| 2020/0187887 | A1 * | 6/2020 | Alon Cohen | .......... A61B 6/037 |

FOREIGN PATENT DOCUMENTS

JP 6234698 B2 * 11/2017 ............. A61B 5/055

\* cited by examiner

*Primary Examiner* — Kiho Kim
(74) *Attorney, Agent, or Firm* — Oblon, McClelland, Maier & Neustadt, L.L.P.

(57) ABSTRACT

According to one embodiment, a nuclear medical diagnostic apparatus includes at least one PET detector module and processing circuitry. The processing circuitry is configured to acquire positional information of the at least one PET detector module based on optical information, and to correct a position of the at least one PET detector module based on the positional information.

10 Claims, 5 Drawing Sheets

US 10,849,572 B2

NUCLEAR MEDICAL DIAGNOSIS APPARATUS AND POSITION CORRECTION METHOD

CROSS-REFERENCE TO RELATED APPLICATIONS

This application claims the benefit of priority of Japanese Patent Application No. 2018-091244, filed May 10, 2018, the entire contents of which are incorporated herein by reference.

FIELD

Embodiments described herein relate generally to a nuclear medical diagnostic apparatus and a position correction method.

BACKGROUND

Recently, along with improvement in spatial resolution of a detector used for a nuclear medical diagnosis apparatus, the positional accuracy required for the detector has been improving. It is expected that a further higher spatial resolution is required for the detector.

In general, the positional accuracy of the detector depends on the processing accuracy and assembling accuracy of the nuclear medical diagnosis apparatus. Accordingly, the cost for securing the positional accuracy tends to increase. For components that influence the positional accuracy, processing accuracy is required. Furthermore, it is required for those components influencing the positional accuracy to withstand deformation such as deflection. For this reason, many metals such as iron are adopted as the components of this type, which leads to an increase in weight of the nuclear medical diagnosis apparatus.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention. The drawings show.

DETAILED DESCRIPTION

Hereinbelow, respective embodiments of a nuclear medical diagnostic apparatus and a position correction method will be described in detail by referring to the accompanying drawings.

In general, according to one embodiment, a nuclear medical diagnostic apparatus includes at least one PET detector module and processing circuitry. The processing circuitry is configured to acquire positional information of the at least one PET detector module based on optical information, and to correct a position of the at least one PET detector module based on the positional information.

Figure 1:
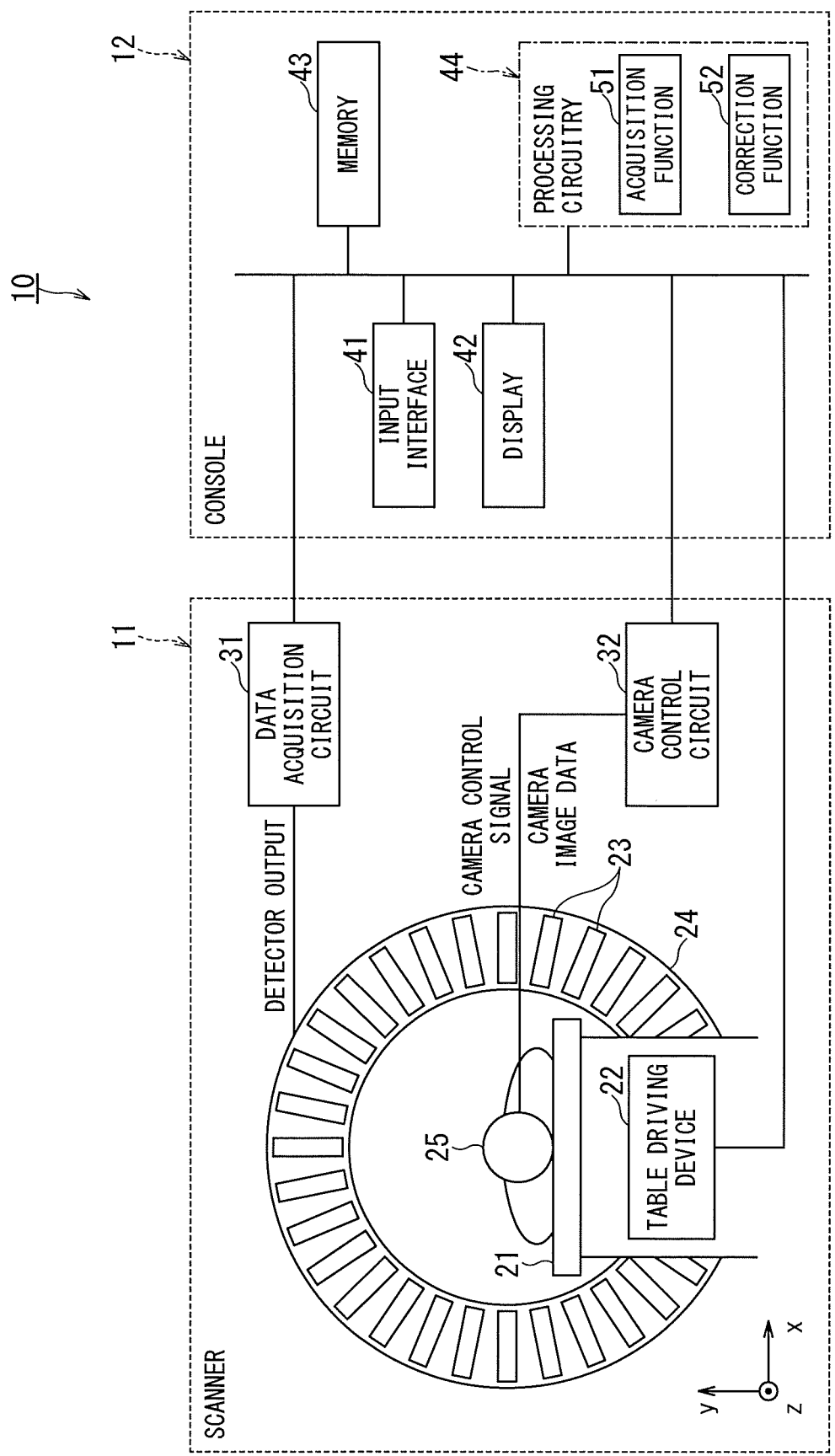
FIG. 1 is a block diagram illustrating a nuclear medical diagnosis apparatus according to one embodiment of the present invention.

FIG. 1 is a block diagram illustrating a nuclear medical diagnosis apparatus 10 according to one embodiment of the present invention. The nuclear medical diagnosis apparatus 10 according to the present embodiment can be applied to an apparatus equipped with a gamma-ray detector such as a PET (Positron Emission Tomography) apparatus and a SPECT (Single Photon Emission Computed Tomography) apparatus. Further, the nuclear medical diagnosis apparatus 10 according to the present embodiment can be applied to a combination apparatus such as a PET-CT apparatus that is a combination of an apparatus having a gamma-ray detector and an X-ray CT (Computed Tomography) apparatus configured to generate a morphological image. Hereinafter, a description will be given of a case where the nuclear medical diagnosis apparatus 10 according to the present invention is configured as the PET apparatus.

The nuclear medical diagnosis apparatus 10 includes a scanner 11 and a console 12. The scanner 11 includes a table 21, a table driving device 22, plural detector modules 23, a PET gantry 24, an optical camera 25, a data acquisition circuit 31, and a camera control circuit 32.

The table 21 is configured such that an object can be placed on the table 21 and the optical camera 25 can be mounted on the table 21.

The table driving device 22 moves the table 21 up and down under the control of the console 12. Further, the table driving device 22 moves the table 21 to the opening of the central portion of the PET gantry 24 along the longitudinal direction (i.e., Z-axis direction) of the table 21 under the control of the console 12.

Each of the detector modules 23 is a detector for detecting gamma-rays emitted from radioactive isotopes that are contained in medicines such as FDG (fluorodeoxyglucose) and are administered to the object.

In the present embodiment, a description will be given of the case where each detector module 23 is a scintillator type detector module. In this case, each detector module 23 includes two-dimensionally arrayed scintillators configured to emit instantaneous light when gamma rays are incident thereon, two-dimensionally arrayed photomultiplier tubes configured to detect the light emitted from the scintillators, a light guide configured to lead the light emitted from the scintillators to the photomultipliers, and an electronic circuit for the scintillators. Each scintillator is constituted by, e.g., thallium activated sodium iodide NaI (Tl). Each time a gamma ray incident event occurs, the electronic circuit for the scintillators uses the outputs of the plural photomultiplier tubes for generating information on the incident position of the gamma rays within the detection plane constituted by the plural photomultiplier tubes and information on intensity of the gamma rays, and outputs the generated information to the data acquisition circuit 31.

In the present embodiment, the plural detector modules 23 are arrayed inside the PET gantry 24 in a hexagonal or circular shape so as to surround the opening of the PET gantry 24, and are ring-array type modules arrayed in a multilayered ring.

Next, a description will be given of the influence of hardware-based displacement (i.e., positional shift) of the detector modules 23 on image quality.

Figure 2:
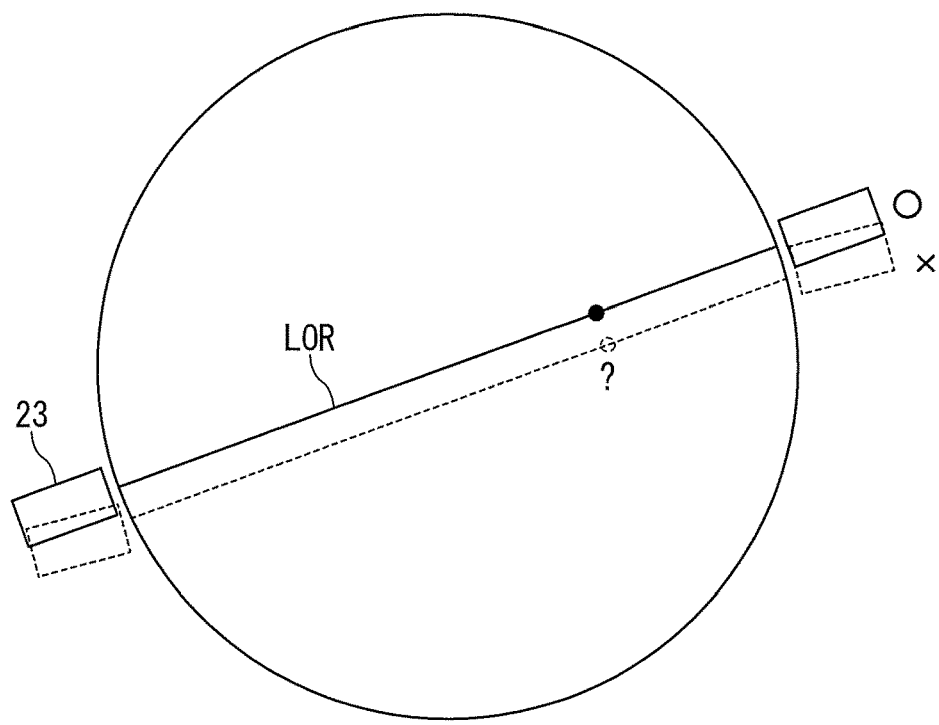
FIG. 2 is a schematic diagram illustrating how image quality is degraded due to displacement of detector modules in terms of hardware.

FIG. 2 is a schematic diagram illustrating how image quality is degraded due to hardware-based displacement of the detector modules 23. In general, the PET apparatus calculates the coordinate point of the occurrence position of the annihilation event by using difference in measurement time between both detector modules which have detected the annihilation event subjected to coincidence counting, and then determines occurrence position information of the annihilation event as distribution blurred by a Gaussian function corresponding to the time resolution of the detectors along the LOR (Line of Response) that is a straight line connecting both detector modules. Thus, the occurrence position of the annihilation event is given as a line segment having a predetermined length along the LOR (Line of Response).

However, when hardware-based displacement occurs in the detector modules 23 such as an error at the time of mounting the detector modules 23 on the PET gantry 24, the LOR is displaced from the positions of the detector modules 23 in the virtual space on the software (the dotted line in FIG. 2) and the spatial resolution deteriorates consequently.

On the other hand, pursuing the positional accuracy of the detector modules 23 in terms of hardware is difficult from the viewpoint of cost, weight, and technical aspects as described above.

For this reason, it is considered to be effective to quantitatively evaluate the hardware-based displacement of the detector modules 23 and remove the influence of the hardware-based displacement on the image quality in terms of software.

In the first place, the influence of the hardware-based displacement of the detector modules 23 on the image quality is attributed to the fact that the positions of the detector modules in the real space are displaced from the positions of the detector modules 23 in the virtual space on the software.

Thus, in order to reduce difference in positional information between both, it is preferable to acquire the positional information of the detector modules 23 in the real space and to use this positional information for correcting the positions of the detector modules 23 in the virtual space or for correcting the positional information in terms of hardware in the real space. In the case of correcting the positional information in terms of hardware, the positions of the detector modules 23 may be adjusted by a driving member such as an actuator.

The nuclear medical diagnosis apparatus 10 according to the present embodiment includes the optical camera 25 for acquiring this positional information. Specifically, the nuclear medical diagnosis apparatus 10 acquires the positional information of the detector modules 23 on the basis of the respective images of the detector modules 23 included in the optical information acquired by the optical camera 25, and corrects the respective positions of the detector modules 23 on the basis of the acquired positional information.

Figure 3:
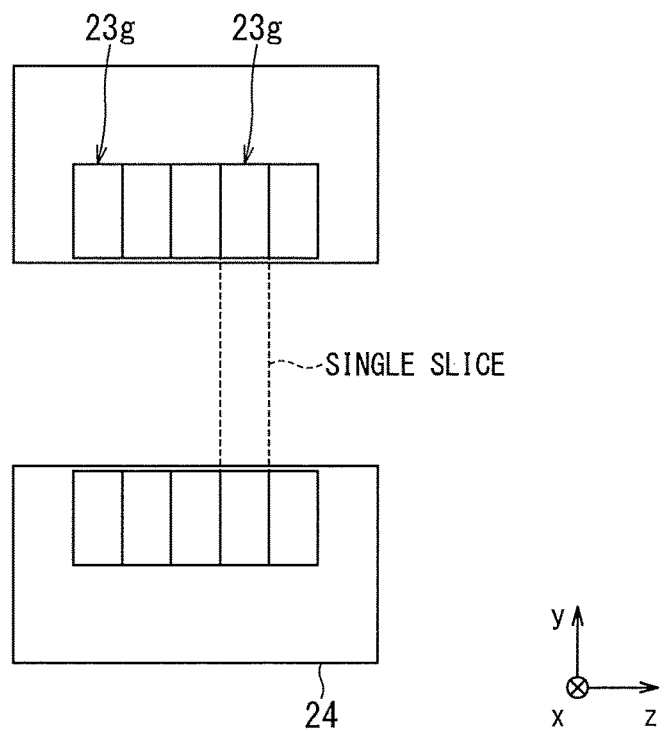
FIG. 3 is a schematic diagram illustrating a module group composed of plural detector modules.

FIG. 3 is a schematic diagram illustrating the module group 23g composed of the plural detector modules 23.

The detector modules 23 constitute one or plural ring-shaped module groups 23g. Hereinafter, each of the ring-shaped module groups 23g is referred to as a slice. When relative positional information between the detector modules 23 can be acquired, degradation of the spatial resolution of the image can be prevented. In order to acquire the relative positional information, it is preferable to acquire an optical camera image for each slice. It is more preferable that parameters of coordinates (x, y, z) and inclination (rx, ry, rz) in the apparatus coordinate space of the nuclear medical diagnosis apparatus 10 can be acquired.

Figure 4A:
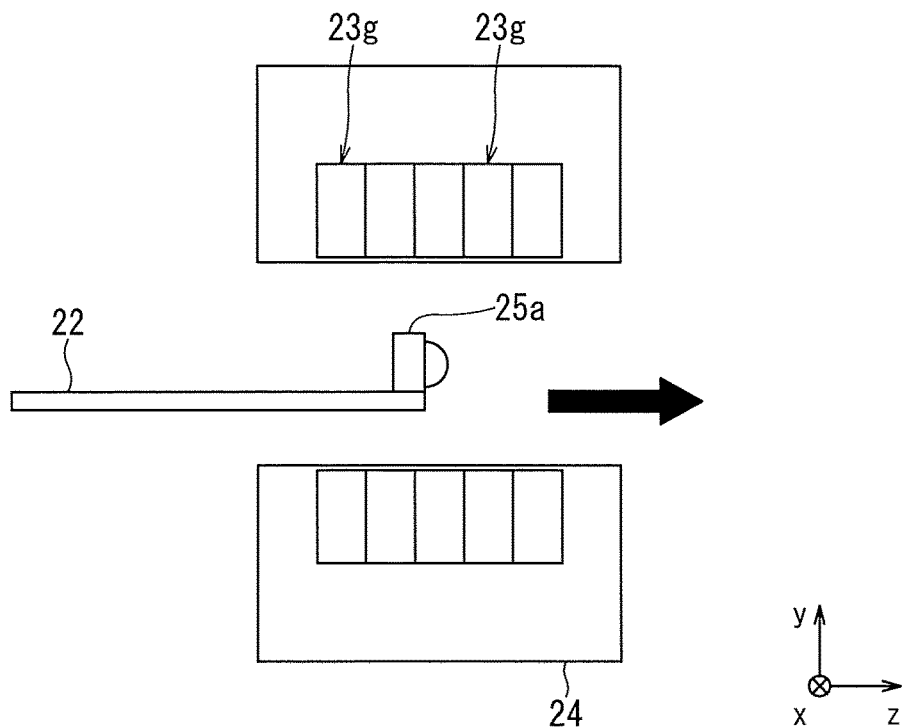
FIG. 4A is a schematic diagram illustrating a case where an optical camera is a celestial camera.

FIG. 4A is a schematic diagram illustrating a case where the optical camera 25 is a celestial camera 25a.

Figure 4B:
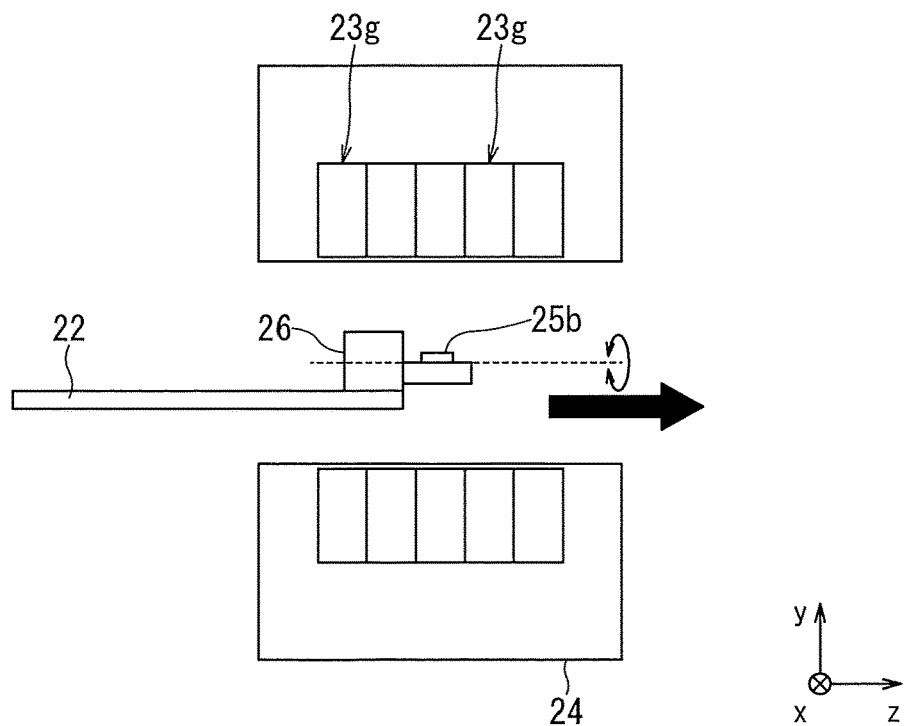
FIG. 4B is a schematic diagram illustrating a case where the optical camera is an ordinary camera.

FIG. 4B is a schematic diagram illustrating a case where the optical camera 25 is an ordinary camera 25b.

When the optical camera 25 is a celestial camera 25a of half-celestial type or omnidirectional type, it is possible to acquire images of the detector modules 23 belonging to the same slice, i.e., belonging to the same module group 23g at a time. More specifically, the celestial camera 25a is attached to the table 21 so as to move integrally with the table 21 and acquires the images of all the module groups 23g by repeating imaging one module group 23g at once, moving a predetermined distance along the Z-axis (i.e., central axis of the ring), and imaging the adjacent module group 23g.

When the optical camera 25 is an ordinary camera 25b to which a special lens such as a wide angle lens is not attached, the ordinary camera 25b may be attached to the table 21 so as to move integrally with the table 21 via a rotation mechanism 26. In this case, the rotation mechanism 26 is constituted by components such as a stepping motor configured to rotate the ordinary camera 25b around the Z-axis, and is controlled by processing circuitry 44 of the console 12 via the camera control circuit 32. At this time, while being rotated around the Z-axis, the ordinary camera 25b repeats imaging of the module group(s) 23g for each rotation of a predetermined angle so as to acquire the entire image of the module group 23g.

Returning to FIG. 1, the console 12 includes an input interface 41, a display 42, a memory 43, and the processing circuitry 44.

The input interface 41 receives various input operations from a user, converts the received input operation into an electric signal, and outputs the electric signal to the processing circuitry 44. For instance, the input interface 41 is realized by components such as a mouse, a keyboard, a trackball, a switch, a button, and a joystick.

The display 42 displays various types of information. For instance, the display 42 outputs a PET image generated by the processing circuitry 44 and a GUI (Graphical User Interface) for receiving various operations from the user. The display 42 is, e.g., a liquid crystal display, a CRT (Cathode Ray Tube) display, or an OLED (Organic Light Emitting Diode) display.

The memory 43 is equipped with a configuration including a processor-readable recording medium such as a hard disk, an optical disk, and a semiconductor memory element, as exemplified by a flash memory and a RAM (Random Access Memory). The memory 43 stores the programs executed by the processing circuitry 44 and other data used by the processing circuitry 44.

The processing circuitry 44 is a processor that executes processing of easily and highly accurately correcting degradation of image quality attributable to hardware-based displacement of the detector modules 23 with the use of the optical information by reading out and executing the programs stored in the memory 43. The processor of the processing circuitry 44 also controls the overall operation of the nuclear medical diagnosis apparatus 10.

As shown in FIG. 1, the processor of processing circuitry 44 implements an acquisition function 51 and a correction function 52. Each of these functions is stored in the memory 43 in the form of a program.

The acquisition function 51 acquires camera images of the detector modules 23 imaged by the optical camera 25, and acquires the positional information of the detector module 23 on the basis of the camera images.

For instance, the acquisition function 51 acquires the positional information of each of the detector modules 23 by performing image processing on the camera image of each module group 23g imaged by the optical camera 25. Specifically, the acquisition function 51 can acquire the distance between the optical camera 25 and each detector module 23 from the size of each detector module 23 included in the camera image, and can obtain the inclination of each detector module 23 with respect to the optical camera 25 from the distortion of each detector module 23 depicted in the camera image.

The correction function 52 corrects the respective positions of the detector modules 23 on the basis of the positional information of each of the detector modules 23 acquired by the acquisition function 51.

In this case, degradation of the spatial resolution of the image can be prevented by correcting the respective positions of the detector modules 23 on the basis of the relative positional information between the detector modules 23. It is more preferable that the respective positions of the detector modules 23 can be corrected on the basis of the parameters of coordinates (x, y, z) and inclination (rx, ry, rz) in the apparatus coordinate space of the nuclear medical diagnosis apparatus 10.

In order to acquire these parameters, information on the reference position is required in addition to the relative positional information. As the reference position, it is possible to use design coordinates of one or plural predetermined detector modules 23 (e.g., detector module 23 that should be at the topmost point of the central slice in the vertical direction). Alternatively or additionally, various positions at which design parameters in the apparatus coordinate space are known in advance can be used as the reference position.

Figure 5:
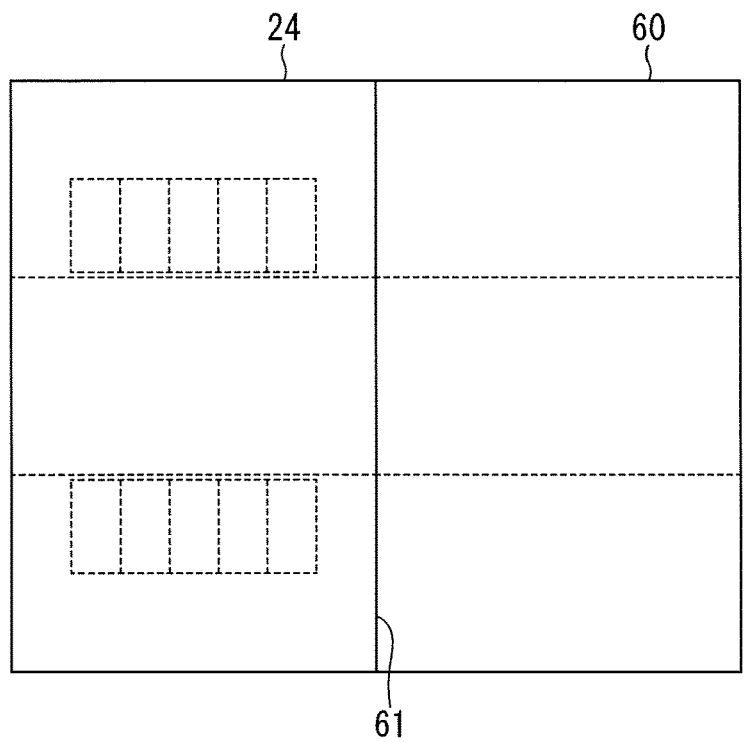
FIG. 5 is a schematic diagram illustrating a case where a CT reference plane is used as a reference position.

FIG. 5 is a schematic diagram illustrating a case where the CT reference plane 61 is used as the reference position. When the nuclear medical diagnosis apparatus 10 is used for a PET-CT apparatus, for instance, the reference position may be set to the CT reference plane 61, which is the mating surface between the PET gantry 24 and the CT gantry 60, to calculate the distance and angle of each detector module. In this case, since the positional relationship between the CT apparatus and the PET apparatus can be accurately grasped, the positioning (i.e., alignment) between the CT image and the PET image can be performed easily and accurately.

In order to enhance the accuracy of image processing, stripe pattern may be applied to either or both of the lens of the optical camera 25 and the respective outer surfaces of the detector modules 23. In the case of applying the stripe pattern to both, the acquisition function 51 can acquire the positional information of each of the detector modules 23 with higher accuracy on the basis of the moire stripe appearing in the camera image. Further, in the case of applying a characteristic coloring or patterning to the respective outer surfaces of the detector modules 23, the acquisition accuracy of the positional information by the acquisition function 51 can be improved. Here, the outer surface means a surface that can be imaged by the optical camera 25.

When the imaging position of the optical camera image in the apparatus coordinate space can be specified on the basis of the optical camera image, the positional information of the detector modules 23 can be determined more accurately.

Figure 6:
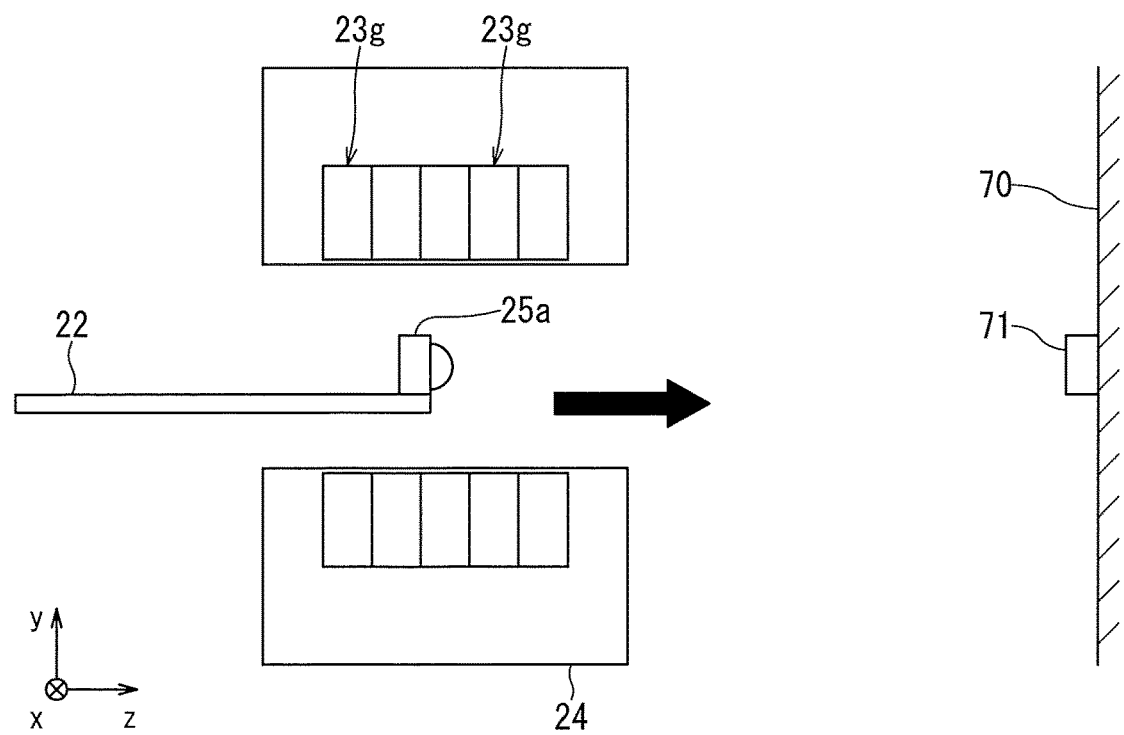
FIG. 6 is a schematic diagram illustrating a marker fixed on a wall surface in the traveling direction of the celestial camera.

FIG. 6 is a schematic diagram illustrating a marker 71 fixed on a wall surface 70 in the traveling direction of the celestial camera 25a.

When the marker 71 is fixed in the imaging region of the celestial camera 25a as shown in FIG. 6, the marker 71 is always depicted in each camera image. In this case, on the basis of the position of the marker 71 in the camera image, it is possible to easily specify the imaging position of the celestial camera 25a as the absolute position in the apparatus coordinate space. Thus, on the basis of the respective images of the module groups 23g and the marker 71 depicted in each camera image, the positional information of each of the detector modules 23 can be accurately acquired.

Additionally, the correction function 52 may calculate a system matrix according to the positional information of each of the detector modules 23 acquired by the acquisition function 51 and use the system matrix for performing iterative reconstruction on the basis of the respective output signals of the detector modules 23.

Figure 7:
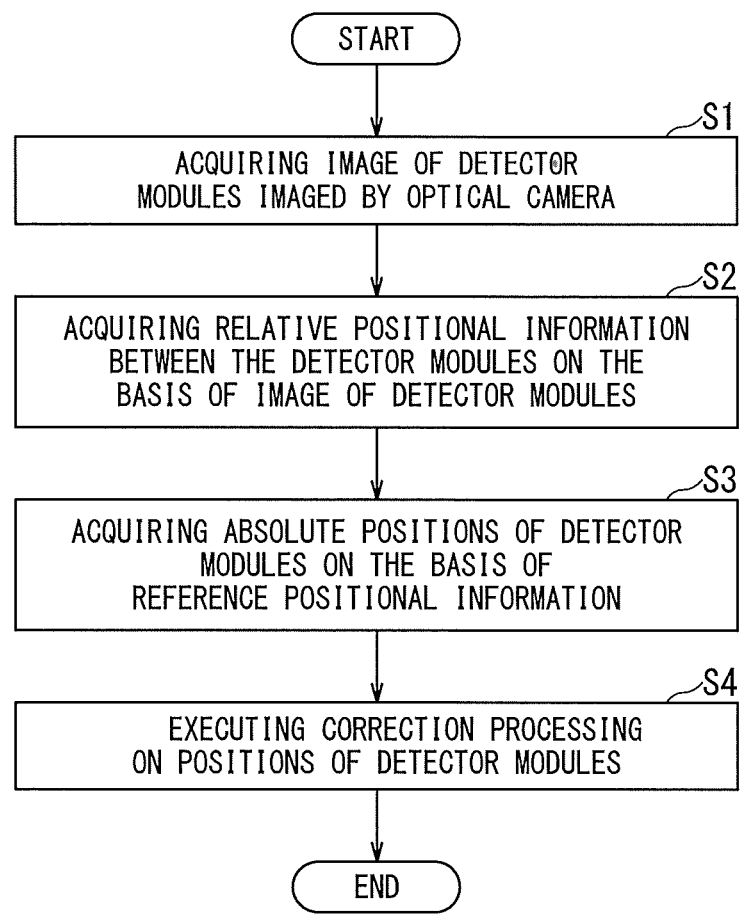
FIG. 7 is a flowchart illustrating a procedure in which the processor of the processing circuitry shown in FIG. 1 easily and highly accurately corrects degradation of image quality caused by hardware displacement of the detector modules on the basis of optical information.

FIG. 7 is a flowchart illustrating a procedure in which the processor of the processing circuitry 44 shown in FIG. 1 easily and highly accurately corrects degradation of image quality caused by hardware-based displacement of the detector modules 23 on the basis of the optical information. In FIG. 7, each reference sign composed of "S" and number on its right side indicates the step number of the flowchart.

This procedure is started at the time of installation of the nuclear medical diagnosis apparatus 10 and is also started at regular maintenance timing such as every morning, every night, or before each time of PET imaging.

First, in the step S1, the acquisition function 51 acquires the respective images of the detector modules 23 imaged by the optical camera 25.

In the next step S2, the acquisition function 51 acquires the relative positional information between the detector modules 23 on the basis of the camera images of the detector modules 23. The above-described procedure makes it possible to perform positional correction based on the relative positional information between the detector modules 23.

When the reference position can be used, in the next step S3, the acquisition function 51 acquires parameters (absolute position) of the detector modules 23 in the apparatus coordinate space on the basis of the reference positional information.

In the next step S4, the correction function 52 executes positional correction processing on the detector modules 23 in terms of software or hardware. According to the above-described procedure, the degradation of the image quality caused by the hardware-based displacement of the detector modules 23 can be easily and highly accurately corrected by using the optical information.

According to the nuclear medical diagnosis apparatus 10 of the present embodiment, the relative positional information between the detector modules 23 can be acquired on the basis of the respective images of the module groups 23g imaged by the optical camera 25. Additionally, the absolute positional information can be acquired by using the reference position. Thus, as compared with the method of improving spatial resolution by a hardware-based approach as exemplified by the use of metal such as iron for the component members, it is possible to correct the displacement with significantly reduced processing cost and assembly cost and to easily and accurately acquire the correction parameters in a short time. Further, as compared with the method of improving spatial resolution by the hardware-based approach as exemplified by the use of metal such as iron for the component members, more lightweight components can be selected, which reduces the overall weight of the apparatus and facilitates transportation and installation of the nuclear medical diagnosis apparatus 10.

According to at least one embodiment described above, degradation of image quality caused by hardware-based displacement of the detector modules 23 can be easily and highly accurately corrected by using the optical information.

The processing circuitry in the above-described embodiments is an example of the processing circuitry described in the claims. In addition, the term "processor" used in the explanation in the above-described embodiments, for instance, refer to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing corresponding program. When a plurality of processors are provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medical diagnosis apparatus comprising:
    at least one PET detector module; and
    processing circuitry configured to
        acquire positional information of the at least one PET detector module based on optical information, and
        correct a position of the at least one PET detector module based on the positional information.

2. The nuclear medical diagnosis apparatus according to claim 1, wherein
    the at least one PET detector module comprises a plurality of PET detector modules,
    at least one ring-shaped module group is configured by arranging the plurality of PET detector modules in a ring-shape in a gantry,
    the optical information includes an image of each ring-shaped module group imaged at once by a celestial camera, and
    the processing circuitry is configured to acquire the positional information of each of the plurality of PET detector modules based on the image of the each ring-shaped module group.

3. The nuclear medical diagnosis apparatus according to claim 2, wherein
    the at least one ring-shaped module group comprises a plurality of ring-shaped module groups, and
    the celestial camera is configured to acquire a plurality of images each image of which is an image of each of the plurality of ring-shaped module groups, by repeating a series of procedures including imaging one ring-shaped module group at once, moving a predetermined distance along a central axis of the ring, and then imaging an adjacent ring-shaped module group at once.

4. The nuclear medical diagnosis apparatus according to claim 2, further comprising a marker fixed inside an imaging region of the celestial camera,
    wherein the processing circuitry is configured to acquire the positional information of each of the plurality of PET detector modules based on the image of each of the plurality of ring-shaped module groups and an image of the marker, both of which are depicted in an image imaged by the celestial camera.

5. The nuclear medical diagnosis apparatus according to claim 1, wherein
    the at least one PET detector module comprises a plurality of PET detector modules, and at least one ring-shaped module group is configured by arranging the plurality of PET detector modules in a ring-shape in a gantry,
    the optical information includes an image of each ring-shaped module group acquired by rotating a camera around a central axis of the ring and causing the camera to image the each ring-shaped module group each time of rotation of a predetermined angle, and
    the processing circuitry is configured to acquire the positional information of each of the plurality of PET detector modules based on the image of the each ring-shaped module group.

6. The nuclear medical diagnosis apparatus according to claim 2, wherein the processing circuitry is configured to acquire the positional information of each of the plurality of PET detector modules by performing image processing on the each image of the plurality of ring-shaped module groups.

7. The nuclear medical diagnosis apparatus according to claim 1, wherein
    the at least one PET detector module comprises a plurality of PET detector modules, and
    the processing circuitry is configured to perform iterative reconstruction based on respective output signals of the plurality of PET detector modules by using a system matrix that are calculated according to the positional information of each of the plurality of PET detector modules.

8. The nuclear medical diagnosis apparatus according to claim 1, wherein
    the at least one PET detector module comprises a plurality of PET detector modules,
    stripe pattern is applied to either or both of (i) a lens of a camera or a celestial camera outputting the optical information and (ii) respective outer surfaces of the plurality of PET detector modules, and the processing circuitry is configured to acquire the positional information of each of the plurality of PET detector modules based on the stripe pattern included in the optical information.

9. The nuclear medical diagnosis apparatus according to claim 1, wherein the at least one PET detector module comprises a plurality of PET detector modules, coloring or patterning is applied to respective outer surfaces of the plurality of PET detector modules, and the processing circuitry is configured to acquire the positional information of each of the plurality of PET detector modules based on the coloring or patterning included in the optical information.

10. A position correction method comprising:

acquiring positional information of a PET detector module based on optical information; and correcting a position of the PET detector module based on the positional information.

* * * * *